(12) United States Patent
Evans

(10) Patent No.: US 9,131,860 B2
(45) Date of Patent: Sep. 15, 2015

(54) IDENTIFYING THE LEVEL OF FETAL RISK DURING LABOR

(76) Inventor: Mark Evans, Fort Lee, NJ (US)

(*) Notice: Subject to any disclaimer, the term of this patent is extended or adjusted under 35 U.S.C. 154(b) by 1258 days.

(21) Appl. No.: 12/345,090

(22) Filed: Dec. 29, 2008

(65) Prior Publication Data

US 2010/0168528 A1   Jul. 1, 2010

(51) Int. Cl.
*A61B 5/0444* (2006.01)
*A61B 5/024* (2006.01)
*A61B 5/11* (2006.01)
*A61B 5/00* (2006.01)

(52) U.S. Cl.
CPC ......... *A61B 5/02411* (2013.01); *A61B 5/02405* (2013.01); *A61B 5/1107* (2013.01); *A61B 5/4362* (2013.01); *A61B 2503/02* (2013.01)

(58) Field of Classification Search
CPC .. A61B 5/4362; A61B 5/4356; A61B 5/0444; A61B 5/02411
USPC .......................................................... 600/511
See application file for complete search history.

(56) References Cited

U.S. PATENT DOCUMENTS

| | | | |
|---|---|---|---|
| 3,989,034 | A | 11/1976 | Hojaiban |
| 4,821,732 | A | 4/1989 | Lippes |
| 4,951,680 | A | 8/1990 | Kirk et al. |
| 5,069,218 | A | 12/1991 | Ikeda |
| 5,088,497 | A | 2/1992 | Ikeda |
| 5,123,420 | A | 6/1992 | Herrenberg |

(Continued)

FOREIGN PATENT DOCUMENTS

| | | |
|---|---|---|
| EP | 0384339 | 8/1990 |
| EP | 1568316 | 8/2005 |

(Continued)

OTHER PUBLICATIONS

Parer, et al, "A framework for standardized management of intrapartum fetal heart rate patterns", Am. Jour. Obst. & Gyn., Jul. 2007, pp. 26.e1-26.e6.

(Continued)

*Primary Examiner* — Christopher D Koharski
*Assistant Examiner* — Michael D Abreu
(74) *Attorney, Agent, or Firm* — Dickinson Wright PLLC

(57) ABSTRACT

A method for identifying the level of fetal risk during labor comprises monitoring at least each of the concurrent clinical parameters of (a) FHR, (b) baseline FHR variability, (c) FHR accelerations, (d) FHR decelerations, and (e) maternal uterine activity, to determine whether each parameter independently exhibits at least one non-reassuring characteristic, and indicating a present level of risk to the fetus corresponding to the number of the concurrent clinical parameters (a) through (e) that are simultaneously, independently non-reassuring. An apparatus for implementing the method comprises at least one computer operative to receive input signals indicative of at least FHR and maternal uterine activity in a patient. The computer is operative to determine from the FHR baseline FHR variability, FHR accelerations, and FHR decelerations, to determine when any one or more of the parameters (a) through (e) each exhibit at least one non-reassuring characteristic, and to determine a present level of risk to the fetus corresponding to the number of the parameters (a) through (e) that are simultaneously, independently non-reassuring. At least one output operatively connected to the at least one computer indicates the determined present level of risk to the fetus.

25 Claims, 5 Drawing Sheets

(56) References Cited

U.S. PATENT DOCUMENTS

| | | |
|---|---|---|
| 5,425,362 A | 6/1995 | Siker et al. |
| 5,433,204 A | 7/1995 | Olson |
| 5,442,940 A | 8/1995 | Secker et al. |
| 5,474,065 A | 12/1995 | Meathrel |
| 5,497,317 A | 3/1996 | Hawkins |
| 5,511,553 A | 4/1996 | Segalowitz |
| 5,596,993 A | 1/1997 | Oriol |
| 5,623,939 A | 4/1997 | Garfield |
| 5,851,188 A | 12/1998 | Bullard et al. |
| 5,954,663 A * | 9/1999 | Gat .................... 600/511 |
| 5,957,855 A | 9/1999 | Oriol et al. |
| 6,024,701 A | 2/2000 | Almog |
| 6,254,537 B1 | 7/2001 | Nguyen |
| 6,340,346 B1 * | 1/2002 | Almog et al. ............ 600/300 |
| 6,423,016 B1 | 7/2002 | Hamilton |
| 6,434,418 B1 | 8/2002 | Neal et al. |
| 6,522,916 B1 | 2/2003 | Kwon |
| 6,751,498 B1 | 6/2004 | Greenberg et al. |
| 7,113,819 B2 | 9/2006 | Hamilton et al. |
| 7,313,424 B2 | 12/2007 | Mayevsky et al. |
| 7,314,451 B2 | 1/2008 | Halperin et al. |
| 7,333,850 B2 | 2/2008 | Marossero et al. |
| 7,850,625 B2 | 12/2010 | Paltieli |
| 2003/0187364 A1 | 10/2003 | Hamilton et al. |
| 2006/0074329 A1 * | 4/2006 | Ferguson et al. ............ 600/511 |
| 2007/0213627 A1 * | 9/2007 | James et al. ................ 600/511 |
| 2007/0255588 A1 | 11/2007 | Hamilton |

FOREIGN PATENT DOCUMENTS

| | | |
|---|---|---|
| KR | 1020010105460 | 11/2001 |
| WO | WO 98/49942 | 11/1998 |
| WO | WO 00/01117 | 1/2000 |
| WO | WO 2007/120873 | 10/2007 |

OTHER PUBLICATIONS

Parer, JT, "FHR Monitoring: Can we expect improvements soon?", Maternal Fetal Medicine, University of California San Francisco, MFM Fellows Videoconference Series, May 21, 2008.

"Intrapartum fetal heart rate patterns in infants with (>-34 weeks) with poor neurological outcome"; Yuki Kodama, et al. Early Human Development 85 (2009), pp. 235-238.

Fetal Heart Rate Patterns in Neonatal Hypoxic-Ischemic Encephalopathy: Relationship with Early Cerebral Activity and Neurodevelopmental Outcome; Deirdre M. Murray, M.D., et al. American Journal of Peinatology, vol. 26, No. 8 (2009).

* cited by examiner

IDENTIFYING THE LEVEL OF FETAL RISK DURING LABOR

FIELD OF THE INVENTION

The invention pertains to a method and apparatus for identifying the present level of fetal risk during labor by monitoring a number of fetal-risk-related parameters and transforming the number of those parameters that are simultaneously, independently non-reassuring into a corresponding indication of the level of risk to the fetus during labor.

BACKGROUND

It is well-known that when the fetal reserve is decreased, any diminution in maternal cardiac output, oxygenation of the maternal blood, or maternal uterine blood flow will place the fetus at significant subsequent risk for the development of fetal hypoxia and asphyxia (metabolic acidosis) if labor is allowed to continue. It is estimated that, in the United States, 700 infant deaths per year are the result of intrauterine hypoxia and birth asphyxia. It is also widely accepted that fetal neurological injury that develops during labor results from progressive hypoxia and acidemia severe enough to produce cerebral ischemia.

Electronic fetal monitoring (EFM) was introduced in the late 1950's in an attempt to permit timely intervention (e.g., expedited delivery by cesarean section) in situations in which the fetus appears to either be presently compromised already or will be so imminently. EFM has been widely adopted and is currently used in the majority of births in the United States.

EFM allows the early detection of fetal oxygen deprivation leading to hypoxia and metabolic acidosis through the reasonable interpretation of characteristic fetal heart rate (FHR) patterns. Generally speaking, however, the clinical interpretation of fetal heart monitor (FHM) data and interventions based on those interpretations have been quite inconsistent.

Traditionally, when any of the parameters of the FHM data demonstrate "reassurance," labor is allowed to continue, with intervention being reserved for the situation when all of these parameters are abnormal, indicative of significant asphyxia (metabolic acidosis), or an acute emergency arises (e.g., fetal bradycardia). This approach, based on "rescue" of the fetus, has not resulted in improved outcomes either immediately or long-term. To date, there have been several publicized attempts at standardization of EFM interpretation, but deviations are commonplace and interpretation remains very subjective and with little physiological justification. Accordingly, there continues to exist a need for a more standardized interpretation of labor progress and FHR tracings, and which provides for the quantification of these parameters to objectively identify the level of risk for the subsequent development of adverse outcomes such as fetal hypoxia and acidosis if labor is allowed to continue without intervention.

SUMMARY

The specification discloses a method and apparatus for identifying the present level of fetal risk during labor. The method most generally comprises the steps of monitoring in a patient at least each of the concurrent clinical parameters of: (a) FHR, (b) baseline FHR variability, (c) FHR accelerations, (d) FHR decelerations, and (e) maternal uterine activity to determine whether each parameter independently exhibits at least one non-reassuring characteristic; and transforming the number of the parameters (a) through (e) that simultaneously, independently exhibit at least one non-reassuring characteristic into an indication of the present level of risk to the fetus corresponding to the number of the parameters (a) through (e) that simultaneously, independently exhibit at least one non-reassuring characteristic.

According to one aspect of the invention, maternal uterine activity is monitored for the exhibition of at least one non-reassuring characteristic independent of fetal response.

According to a first embodiment of the invention, the highest level of risk to the fetus corresponds to the simultaneous, independent exhibition of at least one non-reassuring characteristic for each of the parameters (a) through (e).

Per another feature of the invention, the presence of non-reassuring characteristics for each of the parameters (a) through (e) is selected from the following:

(a) for FHR: any of (i) a fetal heart rate of over 160 bpm or (ii) a fetal heart rate of less than 120 bpm;

(b) for baseline FHR variability: any of (i) variability of more than 15 bpm or (ii) a variability of less than 5 bpm;

(c) for FHR accelerations: any of (i) the occurrence of less than two accelerations in 10 minutes of 15 bpm for at least 15 seconds, (ii) the absence of shoulders, or (iii) the presence of overshoots;

(d) for FHR decelerations: any of (i) late decelerations, (ii) variable decelerations with slow return to baseline FHR, (iii) the presence of overshoots, or (iv) prolonged FHR deceleration; and (e) for maternal uterine activity: any of (i) repetitive contractions in excess of 5 uterine contractions in 3 consecutive 10 minute windows, (ii) a uterine resting tone of greater than 25 mm Hg, (iii) a contraction duration of greater than 90 seconds, (iv) the coupling or tripling of contractions prior to return to baseline, or (v) a contraction duty cycle of greater than 50%.

According to one feature thereof, the method further comprises the step of identifying a predetermined action to be taken in response to the indicated present level of risk to the fetus.

The inventive method may further comprise the step of identifying the presence in the patient of one or more antecedent clinical parameters which elevate the level of fetal risk during labor. Accordingly, the transforming step comprises transforming the number of the concurrent clinical parameters (a) through (e) that simultaneously, independently exhibit at least one non-reassuring characteristic and the identified number of one or more antecedent clinical parameters which elevate the level of fetal risk during labor into an indication of the present level of risk to the fetus corresponding to the number of the concurrent clinical parameters (a) through (e) that simultaneously, independently exhibit at least one non-reassuring characteristic and the identified number of one or more antecedent clinical parameters which elevate the level of fetal risk during labor.

According to this embodiment, the highest level of risk to the fetus corresponds to any combination of any number of the parameters (a) through (e) that simultaneously, independently exhibit at least one non-reassuring characteristic and any number of the identified number of one or more antecedent clinical parameters which totals 6.

The one or more antecedent clinical parameters may comprise maternal and/or fetal clinical parameters. Maternal antecedent clinical parameters may include one or more selected from the group consisting of hypertension, anemia, hemoglobinopathies, cardiac dysfunction, and maternal pulmonary disorders. Fetal antecedent clinical parameters may include one or more from the group consisting of prematurity, IUGR, meconium passage, placental abruption, multiple gestation, and fetal infection resulting in the fetal inflammatory response syndrome (FIRS).

Per another feature of the invention, the one or more antecedent clinical parameters may comprise genetic, proteomic, and metabolic markers correlated to a higher risk of neonatal encephalopathy and cerebral palsy.

Per a further feature of the inventive method, the monitoring step may further comprise monitoring a patient for one or more of the additional concurrent clinical parameters selected from the group of (f) prolonged latent phase, (g) arrest and protraction of the active phase, (h) failed descent of the presenting part, (i) arrested descent of the presenting part, and (j) protracted descent of the presenting part. Accordingly, the transforming step comprises transforming the number of the concurrent clinical parameters (a) through (e) that simultaneously, independently exhibit at least one non-reassuring characteristic and the number of the concurrent clinical parameters (f) through (j) that are simultaneously present in the patient into an indication of the present level of risk to the fetus corresponding to the number of the parameters (a) through (e) that simultaneously, independently exhibit at least one non-reassuring characteristic and the number of the concurrent clinical parameters (f) through (j) that are simultaneously present. According to this embodiment, the highest level of risk to the fetus corresponds to any combination of any number of the parameters (a) through (e) that simultaneously, independently exhibit at least one non-reassuring characteristic and any number of the concurrent clinical parameters (f) through (j) totaling six.

Monitoring a patient for one or more of the additional concurrent clinical parameters (f) through (j) may be combined with, or used alternatively to, the step of identifying the presence in the patient of one or more antecedent clinical parameters which elevate the level of fetal risk during labor. When combined, the transforming step of the inventive method comprises transforming the number of the concurrent clinical parameters (a) through (e) that simultaneously, independently exhibit at least one non-reassuring characteristic, the number of the concurrent clinical parameters (f) through (j) that are simultaneously present in the patient, and the identified number of one or more antecedent clinical parameters which elevate the level of fetal risk during labor into an indication of the present level of risk to the fetus corresponding to the number of the parameters (a) through (e) that simultaneously, independently exhibit at least one non-reassuring characteristic, the number of the concurrent clinical parameters (f) through (j) that are simultaneously present, and the identified number of one or more antecedent clinical parameters which elevate the level of fetal risk during labor. Per this embodiment of the invention, the highest level of risk to the fetus corresponds to any combination of any number of the parameters (a) through (e) that simultaneously, independently exhibit at least one non-reassuring characteristic, any number of the concurrent clinical parameters (f) through (j), and any number of the identified number of one or more antecedent clinical parameters totaling six.

An exemplary apparatus for implementing the inventive method comprises at least one computer operative to receive input signals indicative of at least FHR and maternal uterine activity in a patient. The at least one computer is further operative to determine from the FHR baseline each of FHR variability, FHR accelerations, and FHR decelerations, to determine when any one or more of at least (a) FHR, (b) baseline FHR variability, (c) FHR accelerations, (d) FHR decelerations, and (e) maternal uterine activity each exhibit at least one non-reassuring characteristic, and to determine a present level of risk to the fetus corresponding to the number of the said parameters (a) through (e) that are simultaneously, independently non-reassuring. At least one output is operatively connected to the at least one computer for indicating the present level of risk to the fetus.

Per one feature of the invention, the at least one computer is operative to determine when maternal uterine activity exhibits at least one non-reassuring characteristic independent of fetal response.

Per another feature, the at least one computer may be further operative to identify a predetermined action to be taken in response to the indicated present level of risk to the fetus.

The at least one computer may be further operative to receive user-inputs corresponding to the presence in a patient of one or more antecedent clinical parameters which elevate the level of fetal risk during labor. According to this embodiment, the computer is operative to determine a present level of risk to the fetus corresponding to the number of the one or more antecedent clinical parameters which elevate the level of fetal risk during labor and the number of the parameters (a) through (e) that are simultaneously, independently non-reassuring. Alternatively, or in addition to, the foregoing, the at least one computer may be further operative to receive user-inputs indicative of the presence in the patient of one or more of the concurrent clinical parameters of (f) prolonged latent phase, (g) arrest and protraction of the active phase, (g) failed descent of the presenting part, (i) arrested descent of the presenting part, and (j) protracted descent of the presenting part, the at least one computer is further operative to determine a present level of risk to the fetus corresponding to the number of the parameters (a) through (e) that are simultaneously, independently non-reassuring and the number of the concurrent clinical parameters (f) through (j) that are simultaneously present. This feature may be combined with, of employed in the alternative to, the further feature of receiving user-inputs corresponding to the presence in a patient of the one or more antecedent clinical parameters which elevate the level of fetal risk during labor.

BRIEF DESCRIPTION OF THE DRAWINGS

The present invention will be appreciated from the following description and accompanying drawings, of which.

WRITTEN DESCRIPTION

Figure 1:
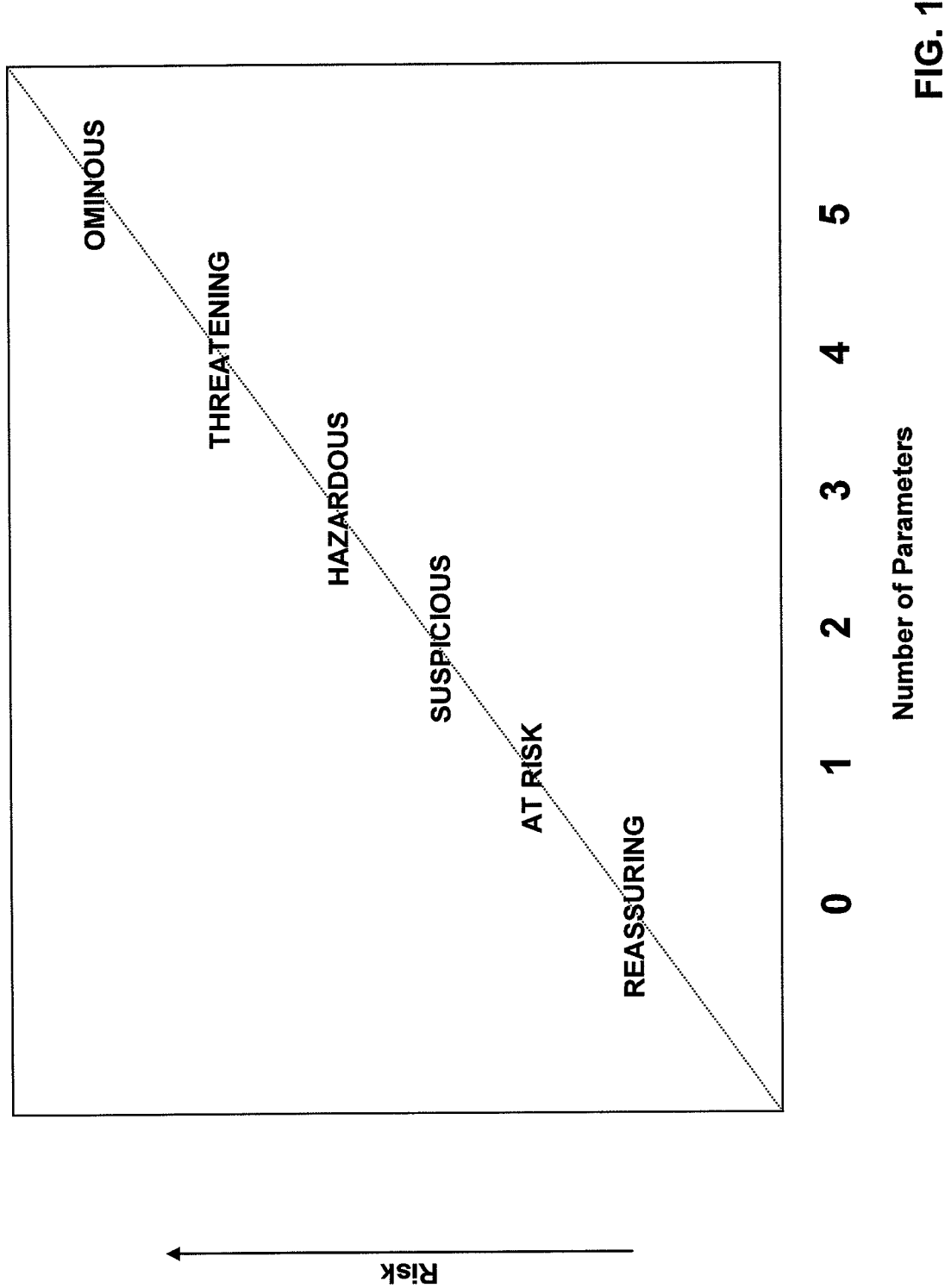
FIG. 1 is a graph depicting an exemplary system for transforming the number of the clinical parameters into an indication of the present level of risk to the fetus.

As required, detailed embodiments of the present invention are disclosed herein. However, it is to be understood that the disclosed embodiments are merely exemplary of the invention that may be embodied in various and alternative forms.

The accompanying drawings are not necessarily to scale, and some features may be exaggerated or minimized to show details of particular components. Therefore, specific structural and functional details disclosed herein are not to be interpreted as limiting, but merely as a representative basis for teaching one skilled in the art to variously employ the present invention.

Referring now to the drawings, there is disclosed a method and apparatus for objectively determining and identifying fetal risk during labor. The method most generally comprises the steps of monitoring each of at least the concurrent clinical parameters of (a) FHR, (b) baseline FHR variability, (c) FHR accelerations, (d) FHR decelerations, and (e) maternal uterine activity (i.e., contractions) to determine whether each parameter independently exhibits at least one non-reassuring characteristic; and transforming the number of the concurrent clinical parameters (a) through (e) that simultaneously, independently exhibit at least one non-reassuring characteristic into an indication of the present level of risk to the fetus corresponding to the number of the parameters (a) through (e) that simultaneously, independently exhibit at least one non-reassuring characteristic.

Preferably, the parameter of maternal uterine activity (e) is monitored for the exhibition of at least one non-reassuring characteristic independent of fetal response.

As exemplified herein in the described embodiments of the invention, correspondence between the number of parameters that simultaneously, independently exhibit at least one non-reassuring characteristic and the indication of the present level of risk to the fetus is preferably, though not necessarily, a one-to-one correspondence. Thus, for instance, the highest level of risk to the fetus according to the method at its most essential (i.e., monitoring the parameters (a) through (e)) corresponds to the simultaneous, independent exhibition of at least one non-reassuring characteristic for each of the parameters (a) through (e), while the lowest level of risk to the fetus corresponds to the absence of any exhibited non-reassuring characteristics for any of these parameters.

As used herein, "concurrent clinical parameters" means and refers to patient (mother and fetus)-related parameters, such as FHR, which are monitored for development or occurrence during (i.e., concurrently with) labor and delivery. "Antecedent clinical parameters," by contrast, means and refers to patient (mother and/or fetus)-related factors preceding a patient's presentation for labor and delivery and the presence of which predisposes a patient to an increased level of fetal risk during labor. Without limitation, such antecedent parameters include the maternal factors of hypertension, anemia, hemoglobinopathies, cardiac dysfunction, and pulmonary disorders, and the fetal factors of prematurity, IUGR, meconium passage, placental abruption, multiple gestation, and fetal infection resulting in FIRS.

According to the present invention, at least the foregoing concurrent clinical parameters (a) through (e) are each monitored for the independent exhibition of any one or more known characteristics of non-reassurance (i.e., signs from EFM and uterine contraction data that the fetal environment is potentially abnormal), such as, by way of non-limiting example, those set forth in Table I below.

TABLE I

| Parameter | Characteristics of Non-Reassurance |
| --- | --- |
| FHR | >160 bpm (tachycardia); or |
|  | <120 bpm (bradycardia) |

TABLE I-continued

| Parameter | Characteristics of Non-Reassurance |
| --- | --- |
| Baseline FHR Variability | >15 bpm; or |
|  | <5 bpm |
| FHR Accelerations | Non-Reactive pattern (<2 accelerations in 10 mins of 15 bpm for 15 secs); or |
|  | Absence of shoulders; or |
|  | Presence of overshoots |
| FHR Decelerations | Late decelerations; or |
|  | Variable decelerations with slow return to baseline FHR; or Presence of overshoots; or |
|  | Prolonged FHR deceleration |
| Maternal Uterine Activity | Repetitive contractions in excess of 5 uterine contractions in 3 consecutive 10 minute windows; or |
|  | Elevated uterine resting tone (i.e., >25 mm Hg); or |
|  | Contraction duration of >90 seconds; or |
|  | Coupling or tripling of contractions prior to return to Baseline; or |
|  | A contraction duty cycle of greater than 50% |

The present invention comprehends monitoring (including via conventional means) at least the specified clinical parameters (a) through (e) for demonstration of one or more non-reassuring fetal characteristics (such as identified in Table I, above) and indicating a present level of risk to the fetus corresponding to the number of these parameters that are simultaneously, independently non-reassuring. To this end, the invention further comprehends, according to the exemplary embodiment, a straightforward and objective system or scheme by which a present level of risk to the fetus is indicated, such as for the clinician, as monitoring proceeds so as to provide an indication of when intervention according to known techniques may be required, or when, in the alternative, continued observation is permissible. According to a first exemplary embodiment of this system (FIG. 1), wherein the highest level of risk to the fetus corresponds to the simultaneous, independent exhibition of at least one non-reassuring characteristic for each of the parameters (a) through (e), each of parameters (a) through (e) is weighted equally in its contribution to the determined level of risk. Thus, the level of risk to the fetus is deemed "reassuring" when no parameter presently displays any non-reassuring characteristics. When any single parameter (a) through (e) exhibits any non-reassuring characteristic, on the other hand, the level of risk increases to "at risk"; when any two parameters (a) through (e) exhibit any non-reassuring characteristic, the level of risk increases to "suspicious"; and so on, all as indicated in FIG. 1, where each number 1 through 5 on the x-axis corresponds to the number of parameters (a) through (e) simultaneously exhibiting any non-reassuring characteristic.

Of course, the particular terms (e.g., "reassuring," "at risk," etc.) or other identifiers assigned to the various levels of risk as outlined above are intended to be exemplary only.

The present invention further contemplates the indication of the type or types of action required for the various identified levels of risk. These types of actions are conventional in nature, as exemplified below, their performance being known to and well within the capacity of those skilled in the art. Furthermore, it will be appreciated that the types of actions specified herein are exemplary only. It is contemplated that to the extent the invention as employed provides an indication of the type or type of action required for a given level of risk, those actions may be different from those specified herein, subject only to the requirement that such actions be consistent with the interests of the patient (mother and fetus).

Still referring to FIG. 1, in the absence of any present exhibition of non-reassuring characteristics for all of the monitored parameters (the "reassuring" identifier, where the number of parameters (a) through (e) is 0) there is deemed to exist no cognizable risk to the fetus. At this stage, no action is required/recommended under the exemplary scheme. The presence of any non-reassuring characteristic(s) for any one of the monitored parameters represents the potential for risk and is thus indicated as creating an "at risk" condition for the fetus. At this juncture, it is recommended that the clinician's attention to the potential need for intervention in a normal vaginal delivery should be heightened. For any two of the parameters, the simultaneous and independent exhibition of any non-reassuring characteristics elevates the fetal risk to "suspicious." This should further heighten the clinician's attention. When any three parameters simultaneously demonstrate non-reassuring characteristics, the risk to the fetus becomes "hazardous" and, at this juncture, the primary caregiver should be present at the patient's bedside to manage the labor. Furthermore, at this level of risk it is recommended that consideration be given to intervention in delivery. When any four of the monitored parameters (a) through (e) simultaneously and independently demonstrate non-reassuring characteristics (risk to the fetus is identified as "threatening"), the clinician should be directed to engage in close observation of the patient and give urgent consideration to delivery. When all five of the monitored parameters (a) through (e) simultaneously and independently demonstrate non-reassuring characteristics (risk to the fetus is identified as "ominous"), immediate resuscitation or intervention is deemed necessary according to known techniques, such as amnioinfusion, discontinuance of agents associated with uterine contractions (e.g., pitocin, prostaglandins, etc.), or performance of operative delivery with forceps, vacuum, by cesarean section, etc.

Of course, it will be understood that the indicated type of action is intended to serve as a guideline only, and not to necessarily replace the independent judgment of the physician or other primary caregiver.

It is contemplated that, in addition to the five monitored concurrent clinical parameters (a) through (e) identified previously (FHR, baseline FHR variability, FHR accelerations, FHR decelerations, and maternal uterine activity), the method may further comprehend the step of identifying the presence in the patient (mother and/or fetus) of one or more antecedent clinical parameters which elevate the level of fetal risk during labor, and therefore indicating a level of risk to the fetus corresponding to the identified number of one or more antecedent clinical parameters which elevate the level of fetal risk during labor and the number of monitored concurrent clinical parameters (a) through (e) that are simultaneously, independently non-reassuring.

These antecedent (medical) clinical parameters may comprise maternal and/or fetal clinical parameters that negatively impact uterine blood flow, fetal oxygenation and tolerance to the stresses of labor. Exemplary maternal antecedent clinical parameters include hypertension (elevated mean blood pressure), anemia and hemoglobinopathies (decreased blood oxygen carrying capacity), cardiac dysfunction (decreased cardiac output), and maternal pulmonary disorders (decreased maternal oxygenation). Exemplary fetal antecedent clinical parameters include extreme prematurity (<28 weeks gestation), IUGR, meconium passage, placental abruption, multiple gestation, and fetal infection resulting in FIRS.

Still other relevant antecedent clinical parameters that can be factored into the methodology of this invention are known genetic, proteomic, and metabolic markers that are associated with higher risk of neonatal encephalopathy and cerebral palsy.

According to the inclusion of such antecedent clinical parameters, the presence of any one will increase the identified level of fetal risk. Per this embodiment, it is contemplated that the highest level of risk to the fetus corresponds to any combination of any number of the parameters (a) through (e) that simultaneously, independently exhibit at least one non-reassuring characteristic and any number of the identified number of one or more antecedent clinical parameters which together total six (as opposed to the five parameters of the aforedescribed embodiment of FIG. 1).

Figure 2:
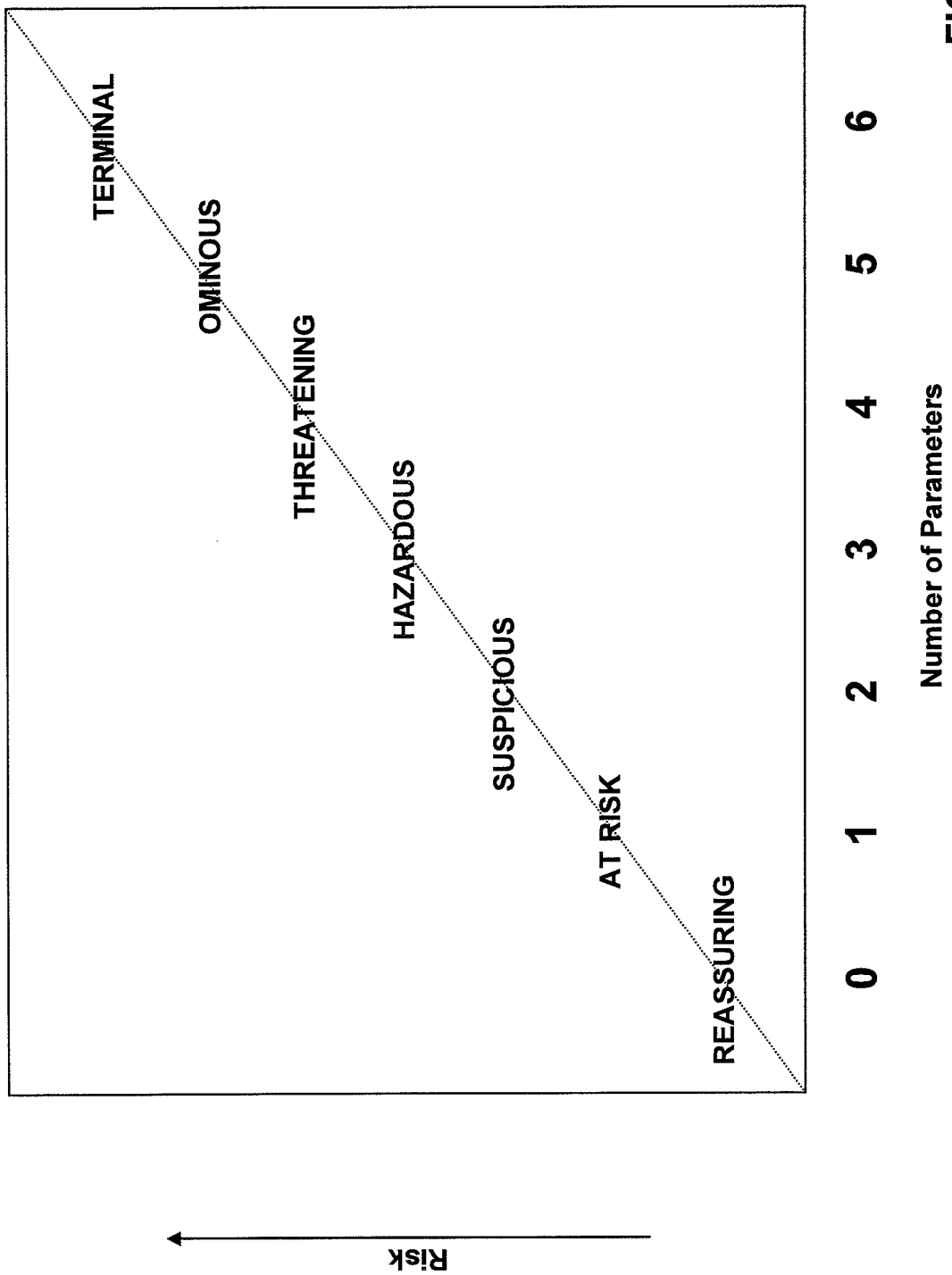
FIG. 2 is a graph depicting an exemplary system, according to alternative embodiments, for transforming the number of the clinical parameters into an indication of the present level of risk to the fetus.

As with the method described above in relation to FIG. 1, each concurrent clinical parameter (a) through (e) exhibiting any non-reassuring characteristic and each identified antecedent clinical parameter is preferably weighted equally in the determination of the level of risk to thereby provide an indication of the level of risk to the fetus corresponding to the number of parameters which are present in the patient/simultaneously non-reassuring. Thus, the level of risk to the fetus is deemed "reassuring" when no parameter presently displays any non-reassuring characteristics and no antecedent clinical parameters have been identified in the patient. When, on the other hand, any single parameter (a) through (e) exhibits any non-reassuring characteristic or any single identified antecedent clinical parameter is present in a patient, the level of risk increases to "at risk"; when any two parameters (a) through (e) exhibit any non-reassuring characteristic, the level of risk increases to "suspicious"; and so on, all as indicated in FIG. 2, where each number 1 through 6 on the x-axis corresponds to the number of parameters (a) through (e) simultaneously exhibiting any non-reassuring characteristic and/or the number of each identified antecedent clinical parameter present in the patient.

According to this embodiment of the invention (and with continuing reference to FIG. 2), when any simultaneous combination of five or six of any of the parameters (a) through (e) and any of the antecedent clinical parameters yields an "ominous" or "terminal" result, respectively, the risk to the fetus is deemed to necessitate immediate intervention or resuscitation. Otherwise, it is contemplated that the indicated levels of risk and the identified action to be taken in response to such indicated level of risk for this embodiment is the same as that for the exemplary embodiment of FIG. 1.

It is contemplated that, in addition to the monitored concurrent clinical parameters (a) through (e) identified previously, and optionally in addition to the further identification of the presence in the patient of one or more antecedent clinical parameters, the inventive method may further comprise monitoring a patient for one or more of the additional concurrent clinical parameters, all known to those skilled in the art, selected from the group of (f) prolonged latent phase, (g) arrest and protraction of the active phase, (h) failed descent of the presenting part, (i) arrested descent of the presenting part, and (j) protracted descent of the presenting part.

According to this embodiment, the transforming step of the inventive method comprises transforming the number of the concurrent clinical parameters (a) through (e) that simultaneously, independently exhibit at least one non-reassuring characteristic and the number of the concurrent clinical parameters (f) through (j) that are simultaneously present in the patient into an indication of the present level of risk to the fetus corresponding to the number of the parameters (a) through (e) that simultaneously, independently exhibit at least one non-reassuring characteristic and the number of the concurrent clinical parameters (f) through (j) that are simultaneously present. In general, as the number of concurrent clinical parameters present and/or exhibiting non-reassuring characteristics increases, the feasibility of safe vaginal delivery decreases while the risk to the fetus increases.

According to the inclusion of such further concurrent clinical parameters (f) through (j), the identified presence of any one will increase the identified level of fetal risk. Thus, for example, the identified presence (at any point during labor) in the patient of any one of the additionally monitored concurrent clinical parameters (f) through (j) and the simultaneous exhibition of non-reassuring characteristics for any two or more of the other monitored concurrent clinical parameters (i.e., any two or more of FHR, baseline FHR variability, FHR accelerations, FHR decelerations, and maternal uterine activity) would constitute a determined level of fetal risk of "hazardous."

In this embodiment of the invention, like that of FIG. 2, the highest level of risk to the fetus corresponds to any combination of any number of the parameters (a) through (e) that simultaneously, independently exhibit at least one non-reassuring characteristic and any number of the concurrent clinical parameters (f) through (j) that are simultaneously present in the patient which together totals six. Thus, with reference to FIG. 2, any simultaneous combination of six of any of the parameters (a) through (e) and any number of the concurrent clinical parameters (f) through (j) yields a level of risk of "terminal," which is deemed, according to the indicated action for that level of risk, to necessitate immediate resuscitation or intervention.

To the extent that the method includes identification of the presence in the patient of one or more antecedent clinical parameters as well as monitoring a patient for one or more of the additional concurrent clinical parameters (f) through (j), the transforming step of the inventive method comprises transforming the number of the concurrent clinical parameters (a) through (e) that simultaneously, independently exhibit at least one non-reassuring characteristic, the number of antecedent clinical parameters present in the patient, and the number of the concurrent clinical parameters (f) through (j) that are simultaneously present in the patient into an indication of the present level of risk to the fetus. As previously, the highest level of risk to the fetus according to this exemplary embodiment corresponds to any combination of any number of the parameters (a) through (e) that simultaneously, independently exhibit at least one non-reassuring characteristic, any number of the concurrent clinical parameters (f) through (j), and any number of the identified number of one or more antecedent clinical parameters which together total six. So, for example, and with continuing reference to FIG. 2, the presence in a patient of a single antecedent clinical parameter and one of the concurrent clinical parameters (f) through (j), and the simultaneous exhibition of non-reassuring characteristics for any two of the other monitored concurrent clinical parameters (i.e., any two of FHR, baseline FHR variability, FHR accelerations, FHR decelerations, and maternal uterine activity) would yield a risk of "threatening" under the exemplary scheme.

Of course, it will be understood that there may be circumstances not expressly recited herein, and outside the scope of this invention, when the progress in labor may independently warrant intervention. Such circumstances are known to those skilled in the art.

As noted, identification of the present level of fetal risk is made by considering each included clinical parameter (concurrent and antecedent) independently from the other clinical parameters. Thus, the schemes for identifying a present level of fetal risk that are within the scope of this invention are not, as is the case with some conventional methodologies, the consequence of interdependence between any parameters but, rather, are strictly a function of the number of monitored parameters which are present in a patient and/or simultaneously, but independently, non-reassuring in their exhibited characteristics. Consistent with the foregoing, the inventive method is also distinguished in that it does not take into account the degree of non-reassurance indicated by the one or more characteristics of any monitored parameters. Rather, the parameters are preferably weighted equally so that any exhibition of non-reassurance according to the predetermined non-reassuring characteristic(s) for the parameters (a) through (e) and, as included, the identified presence of the one or more of the concurrent clinical parameters (f) through (j) and/or the identified presence of one or more antecedent clinical parameters, will cause each such parameter to contribute equally to the presently identified level of risk.

It is contemplated that the above-specified methodology may be implemented by an apparatus 10 comprising at least one computer 20 operative to receive input signals, such as from one or more sensors 30 connected to a patient 40, indicative of at least FHR and maternal uterine activity (FIG. 2). The at least one computer 10 is operative to determine from the FHR each of baseline FHR variability, FHR accelerations, and FHR decelerations, to determine when any one or more of at least (a) FHR, (b) baseline FHR variability, (c) FHR accelerations, (d) FHR decelerations, and (e) maternal uterine activity each exhibit at least one non-reassuring characteristic (for instance, the computer may be programmed with the characteristics of non-reassurance for the aforementioned parameters, such as set forth in Table I, and is operative to compare those characteristics with the input signals and determine baseline FHR variability, FHR accelerations, and FHR decelerations data), and to determine a level of risk to the fetus corresponding to the number of the parameters (a) through (e) that are simultaneously, independently non-reassuring, such as according to the scheme heretofore described in relation to FIG. 1. This may be accomplished by the implementation of a simple algorithm which adds the number of said parameters (a) through (e) that are simultaneously, independently non-reassuring, using arbitrarily assigned values (e.g., 1) for each.

At least one output 50 is operatively connected to the at least one computer 10 for indicating the determined present level of risk to the fetus. Operative connection of these various elements 20, 30 and 50, which may be accomplished by any known means, is indicated by bold lines in FIG. 3. The at least one output 50 may comprise, for example, a video display and/or a printer, warning lights (such as, for instance, a plurality of score-specific lights each corresponding to a different level of risk), an audible alarm, etc. It is also contemplated that the apparatus may, alternatively or in addition, be operative to provide other information, including FHR tracings, uterine activity tracings, and/or further information related to the level of risk presently indicated for the fetus, including, by way of non-limiting example, instructions to the clinician or clinicians pertaining to a predetermined action required or recommended for the identified level of risk. Such other information may be provided through the at least one output 50, for example.

Where the apparatus 10 is operative also to take into account one or more antecedent clinical parameters such as those identified previously, the at least one computer 20 is further operative to receive user-inputs (such as via conventional means, like a keyboard, or mouse in combination with a graphical user-interface, for example) indicative of the presence in a patient of one or more such antecedent clinical parameters which elevate the level of fetal risk during labor. Alternatively, data corresponding to the antecedent clinical parameters may be imported via a local or global computer network, such as from a patient's electronic medical records.

According to this embodiment, the at least one computer is further operative to determine, such as in the manner previously described (e.g., a simple algorithm which adds the number of said parameters using arbitrarily assigned values (e.g., 1) for each), a level of risk to the fetus corresponding to the number of the one or more antecedent clinical parameters which elevate the level of fetal risk during labor and the number of the said parameters (a) through (e) that are simultaneously, independently non-reassuring.

Where the apparatus 10 is operative to take into account the presence of one or more of the further concurrent clinical parameters of (f) prolonged latent phase, (g) arrest and protraction of the active phase, (g) failed descent of the presenting part, (i) arrested descent of the presenting part, and (j) protracted descent of the presenting part, the at least one computer 20 is further operative to receive user-inputs (again, for example, such as via conventional means like a keyboard, or mouse in combination with a graphical user-interface) indicative of the presence in the patient of the one or more parameters (f) through (j). The at least one computer is further operative to determine a present level of risk to the fetus corresponding to the number of the parameters (a) through (e) that are simultaneously, independently non-reassuring and the number of the concurrent clinical parameters (f) through (j) that are simultaneously present, also as previously described. As previously, this may be accomplished by the implementation of a simple algorithm which adds the number of said parameters (a) through (e) that are simultaneously, independently non-reassuring, and the number of identified concurrent clinical parameters (f) through (j).

To the extent that the apparatus 10 is operative to take into account both the presence of any one or more of the concurrent clinical parameters (f) through (j) and the antecedent clinical parameters identified previously, the at least one computer 20 is further operative both to receive (e.g., via a keyboard, mouse in combination with a graphical user-interface, etc.) user-inputs indicative of the presence in the patient of the one or more parameters (f) through (j), and to receive user-inputs indicative of the presence in a patient of one or more such antecedent clinical parameters which elevate the level of fetal risk during labor. Furthermore, the computer 20 is operative (such as in the manner heretofore described) to determine a present level of risk to the fetus corresponding to the number of the parameters (a) through (e) that are simultaneously, independently non-reassuring, the number of the concurrent clinical parameters (f) through (j) that are simultaneously present in the patient, and the number of the one or more antecedent clinical parameters present in the patient (mother and/or fetus).

Figure 3:
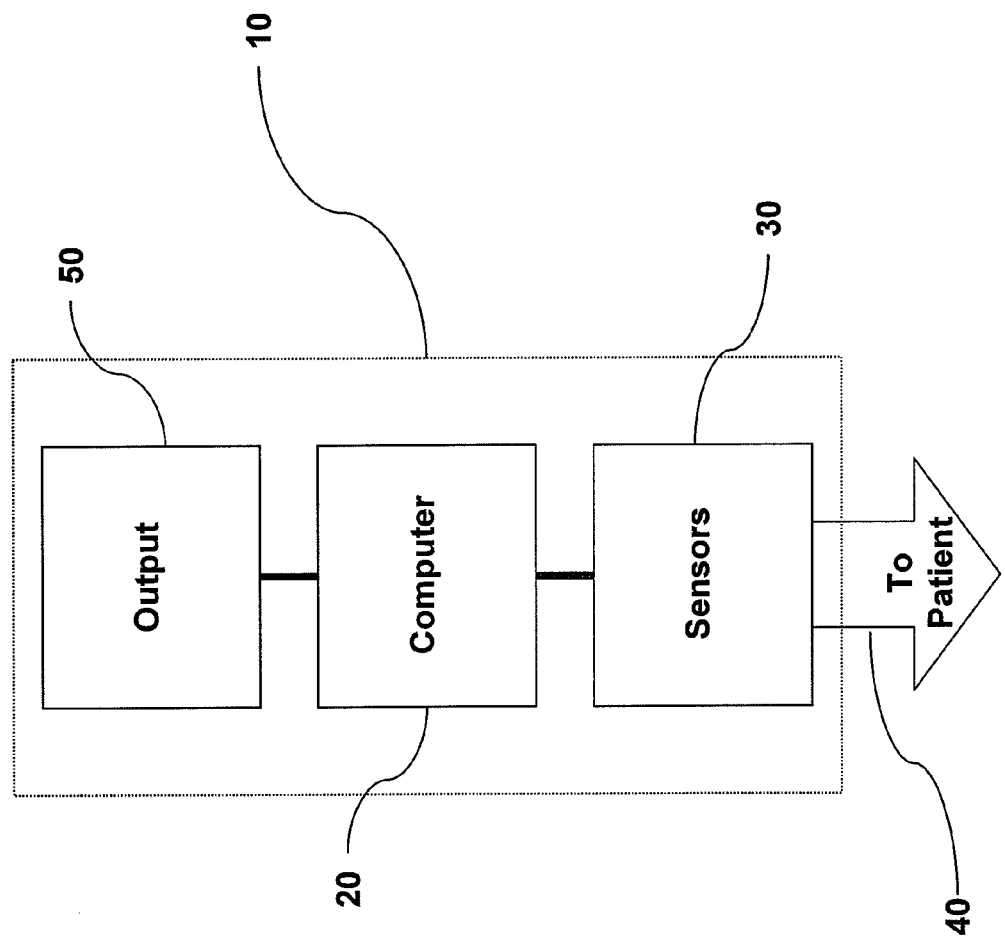
FIG. 3 is a diagrammatic depiction of an exemplary construction for an apparatus for implementing the inventive method.
Figure 4:
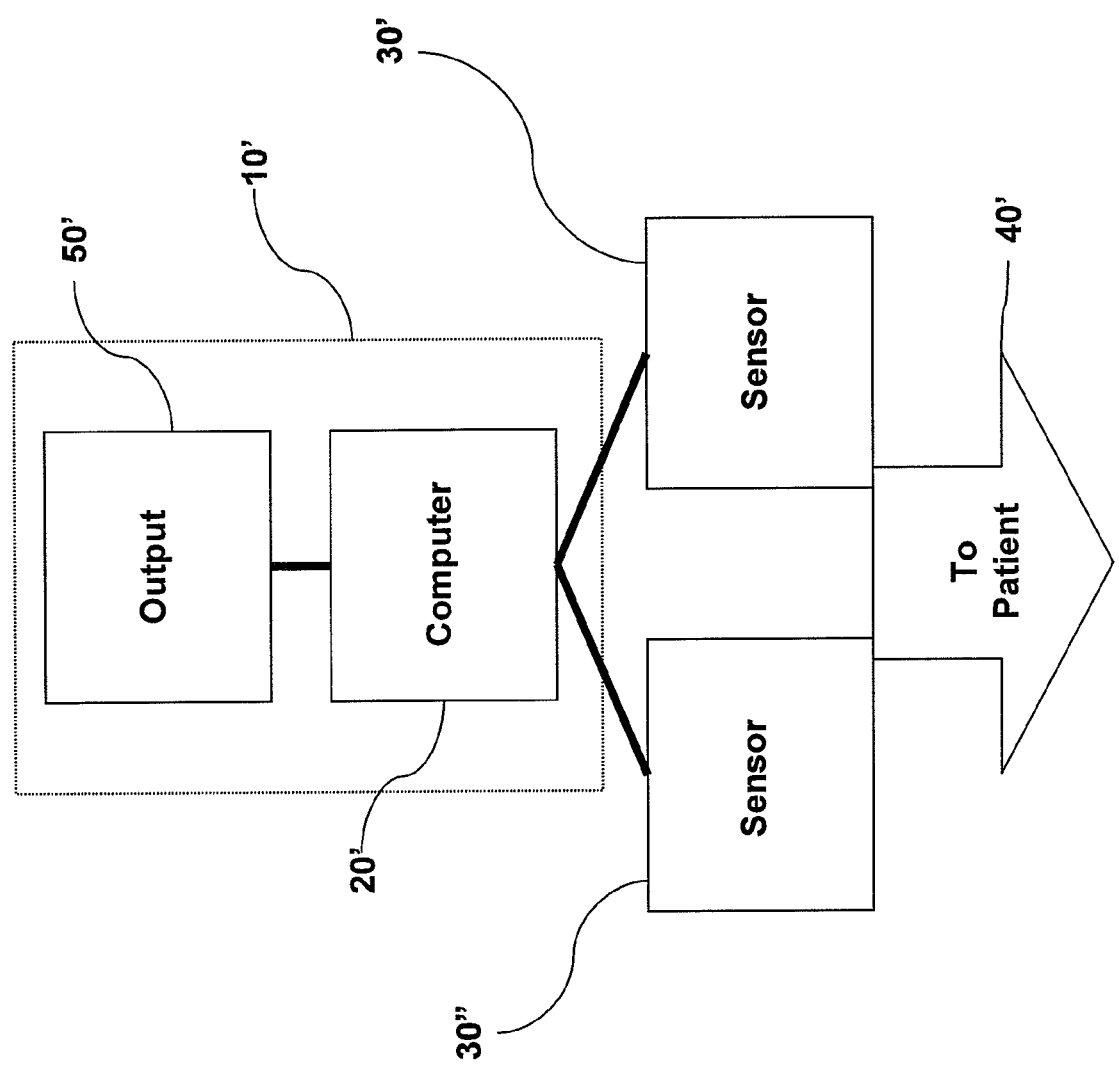
FIG. 4 is a diagrammatic depiction of a second exemplary construction for an apparatus for implementing the inventive method.

It is contemplated that the apparatus 10 may comprise a self-contained unit comprising the one or more sensors 30 capable of monitoring/receiving user-inputs indicative of the aforementioned parameters, such as shown diagrammatically in FIG. 3, or a separate unit 10' which receives inputs corresponding to these parameters from other, separate sensors 30', 30" (FIG. 4). If the former (FIG. 3), the at least one output 50 may, as noted, further be able to provide outputs including one or more of a display and/or printout showing FHR and maternal uterine contraction tracings, such as would be provided with conventional FHM and uterine contraction sensors. If the latter (FIG. 4), the apparatus for implementing the inventive methodology may be a separate apparatus connectable to a FHM device and uterine contraction sensor (each providing their own tracings) and capable of receiving data therefrom.

Figure 5:
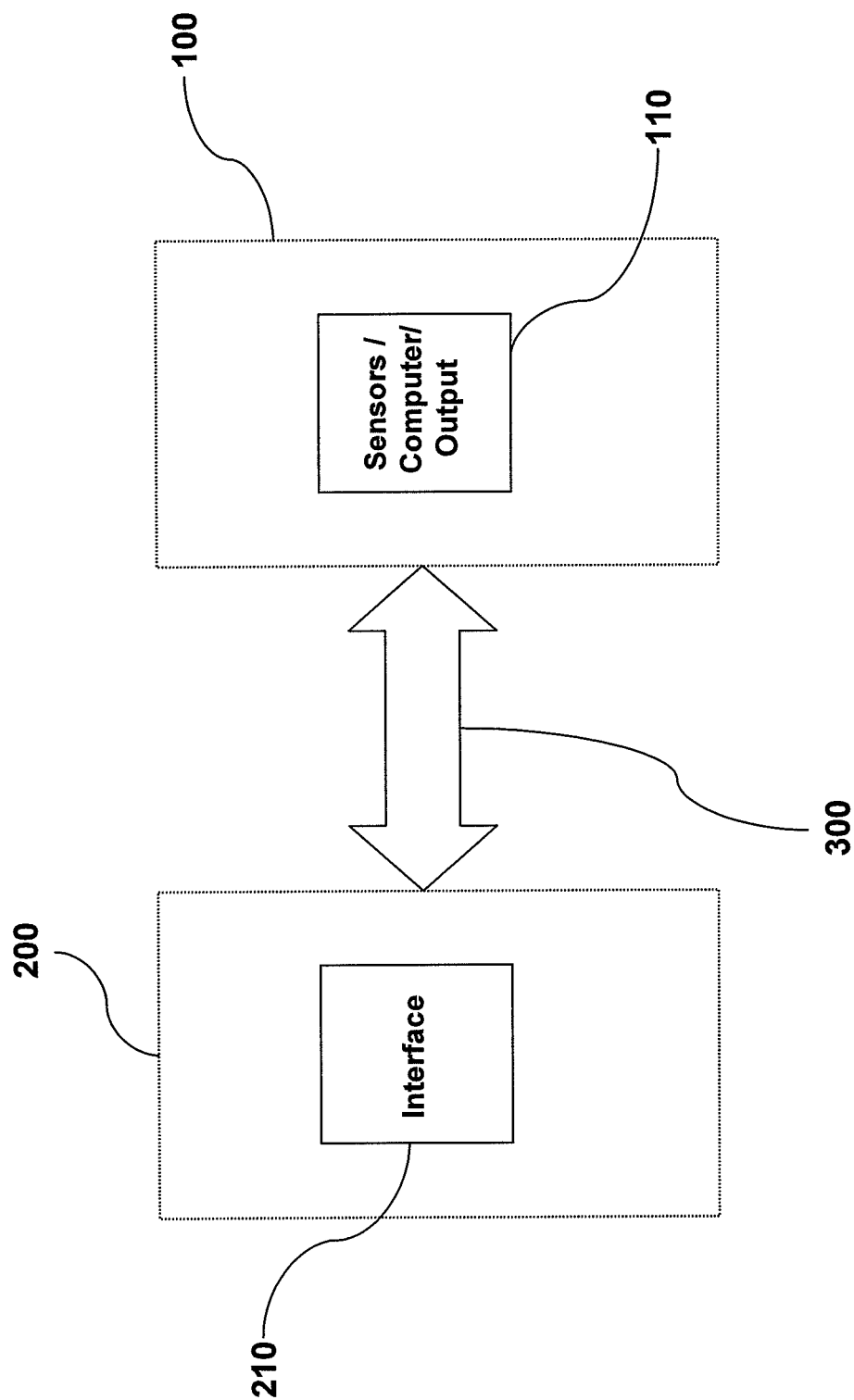
FIG. 5 is a diagrammatic depiction of an embodiment of an apparatus for implementing the inventive method providing for remote monitoring and/or feedback.

According to another embodiment of the inventive apparatus (FIG. 5), the identification of the level of fetal risk can be provided remotely, such as via the internet or other computer network (indicated at 300). According to this embodiment, it is contemplated that one or more persons, such as, for instance, one or more doctors and/or nurses in a geographically remote location 200, are provided a display/interface 210 operatively connected to the apparatus 110 at the site where the patient is located 100, such that the one or more remotely situated persons are presented with the identification of the level of risk to the fetus and, as desired, FHM and uterine contraction tracings and/or other parameters monitored so as to be capable of assisting (including via the interface and/or via other means such as a telephone, video-conference apparatus, etc.) those in the delivery room with the childbirth. For example, this system could be implemented in community hospitals lacking sufficient obstetricians in the delivery room.

In an exemplary implementation, the foregoing or other apparatus operable to perform the inventive method is operatively connected to a patient (either directly or via other monitoring apparatus) to monitor FHR and maternal uterine activity. Continuously or periodically according to a desired schedule, baseline FHR variability, FHR accelerations, and FHR decelerations are determined from the FHR and maternal uterine contraction inputs directly from the patient, and the five parameters (a) through (e) are compared against known characteristics of non-reassurance, such as those specified in Table I, stored in the at least one computer, to determine whether any one or more parameters independently exhibits at least one non-reassuring characteristic. When the at least one computer determines that any non-reassuring characteristics are simultaneously present for any one or more parameters (a) through (e), that determination results in an indication of the corresponding level of risk to the fetus (e.g., "at risk," "suspicious," "hazardous," etc., as heretofore described) via one or more outputs such as warning lights, alarms, a video display, etc. Furthermore, the apparatus will preferably provide an indication of the action required by/recommended for the clinician or other user. For instance, the present simultaneous exhibition of one or more non-reassuring characteristics for any three or more of the monitored parameters (a) through (e) would necessitate the presence of the primary caregiver, such as the attending physician, in the delivery room, as well as notification, for instance via a video display or other output, of impending the need to prepare for possible intervention in the labor. Should it subsequently be determined that any five of the monitored parameters (a) through (e) are simultaneously exhibiting one or more non-reassuring characteristics, notification, for instance via a video display or other output, of the need for immediate resuscitation or other immediate intervention in the labor would be indicated.

To the extent that the apparatus is further operative to take into account any one or more antecedent clinical parameters such as exemplified hereinabove, the apparatus would further provide for the user to specify the existence of any one or more of such parameters in the patient (again, such as via keyboard and/or mouse, via a touchscreen monitor, via dedicated input keys, etc.), preferably prior to, or at least nearly simultaneously with, the commencement of the patient's presentment for labor and delivery. Each such specified antecedent clinical parameter would, according to the exemplary scheme described above, be stored in the at least one computer and serve as a baseline which would contribute to the present level of risk determined by further adding thereto the numbers of any further concurrent parameters (a) through (e). It will be appreciated that, according to this aspect of the invention, a patient exhibiting any antecedent clinical parameters factored into the determination of the level of risk to the fetus will more quickly demonstrate a level of risk (e.g., "at risk," "suspicious," etc.) as fewer monitored concurrent clinical parameters need to exhibit one or more characteristics of non-reassurance/be identified as present in the patient to achieve the same level of risk as a patient exhibiting no such antecedent clinical parameters.

Likewise, to the extent that the apparatus is further operative to take into account any one or more concurrent clinical parameters (f) through (j) such as exemplified hereinabove, the apparatus would further provide for the user to specify the existence of any one or more of such parameters in the patient during the course of labor, such as via keyboard and/or mouse, via a touchscreen monitor, via dedicated input keys, etc. Each such specified clinical parameter (f) through (j) would, according to the exemplary scheme described above, be stored in the at least one computer and would contribute to the present level of risk determined by further adding thereto the numbers of any further concurrent parameters (a) through (e) and, as optionally included, antecedent clinical parameters. It will be appreciated that, according to this aspect of the invention, a patient exhibiting any such further concurrent clinical parameters (f) through (j) factored into the determination of the level of risk to the fetus will more quickly demonstrate a level of risk as fewer concurrent clinical parameters (a) through (e) need to exhibit one or more characteristics of non-reassurance and, as optionally included, fewer antecedent clinical parameters need to be identified in the patient to achieve the same level of risk as a patient exhibiting no such clinical parameters (f) through (j).

By the foregoing, the invention allows for a more standardized interpretation of labor progress and FHR tracings, beneficially takes into consideration the analysis of maternal uterine activity and, optionally, maternal and fetal antecedent clinical parameters which may bear on the level of identified fetal risk during labor, and provides for the quantification of these parameters to objectively, and with consistent repeatability, identify the level of risk for the subsequent development of adverse outcomes such as fetal hypoxia and acidosis if labor is allowed to continue without intervention.

The foregoing description of the exemplary embodiment of the invention has been presented for purposes of illustration and description. It is not intended to be exhaustive or to limit the invention to the precise form disclosed, and modifications and variations are possible in light of the above teachings or may be acquired from practice of the innovation. The embodiments are shown and described in order to explain the principals of the innovation and its practical application to enable one skilled in the art to utilize the innovation in various embodiments and with various modifications as are suited to the particular use contemplated. Although only a few embodiments of the present innovations have been described in detail in this disclosure, those skilled in the art who review this disclosure will readily appreciate that many modifications are possible without materially departing from the novel teachings and advantages of the subject matter recited. Accordingly, all such modifications are intended to be included within the scope of the present innovations. Other substitutions, modifications, changes and omissions may be made in the design, operating conditions and arrangement of the exemplary embodiments without departing from the spirit of the present innovations.

The invention in which an exclusive property or privilege is claimed is defined as follows:

1. An apparatus for identifying the level of fetal risk during labor, comprising:

at least one computer operative to receive input signals indicative of at least fetal heart rate ("FHR") and maternal uterine activity in a patient, the at least one computer further operative (i) to determine from the FHR at least baseline FHR variability, FHR accelerations, and FHR decelerations, and (ii) to determine when each of at least (a) FHR, (b) baseline FHR variability, (c) FHR accelerations, (d) FHR decelerations, and (e) maternal uterine activity exhibit at least one non-reassuring characteristic from among a plurality of pre-defined non-reassuring characteristics for at least the parameters (a) through (e); and wherein the at least one computer is further operative to (iii) receive user-inputs indicative of the presence in the patient of one or more antecedent clinical parameters which elevate the level of fetal risk during labor, and (iv) to determine at a given point in time during labor a present level of risk to the fetus which takes into account only:

the total number of the one or more antecedent clinical parameters which elevate the level of fetal risk during labor; and the total number of the parameters (a) through (e) that each simultaneously, independently exhibit at least one of the non-reassuring characteristics at the given point in time during labor;

wherein the at least one computer is further operative to indicate a predetermined action to be taken in response to the present level of risk to the fetus, and wherein further the indicated predetermined action is intervention in labor when the present level of risk to the fetus for an adverse outcome is at a predetermined level; and at least one output operatively connected to the at least one computer, the at least one output indicating the determined present level of risk to the fetus and the predetermined action to be taken in response to the indicated present level of risk to the fetus.

2. The apparatus of claim 1, wherein the at least one computer is further operative to receive user-inputs indicative of the presence in the patient of the concurrent clinical parameters of (f) prolonged latent phase, (g) arrest and protraction of the active phase, (h) failed descent of the presenting part, (i) arrested descent of the presenting part, and (j) protracted descent of the presenting part, and wherein the at least one computer is operative to determine a present level of risk to the fetus corresponding to the total number of the parameters (a) through (e) that simultaneously, independently exhibit at least one non-reassuring characteristic and the number of the concurrent clinical parameters (f) through (j) that are simultaneously present.

3. The apparatus of claim 2, wherein the highest determined level of risk to the fetus corresponds to any combination of a number of the parameters (a) through (e) that simultaneously, independently exhibit at least one non-reassuring characteristic and a number of the concurrent clinical parameters (f) through (j) that are simultaneously present in the patient which together total six.

4. The apparatus of claim 2, wherein the at least one computer is further operative to identify a predetermined action to be taken in response to the indicated present level of risk to the fetus.

5. The apparatus of claim 1, wherein the one or more antecedent clinical parameters are maternal antecedent clinical parameters.

6. The apparatus of claim 5, wherein the maternal antecedent clinical parameters are one or more from the group consisting of hypertension, anemia, hemoglobinopathies, cardiac dysfunction, and maternal pulmonary disorders.

7. The apparatus of claim 1, wherein the one or more antecedent clinical parameters are fetal antecedent clinical parameters.

8. The apparatus of claim 7, wherein the fetal antecedent clinical parameters are one or more from the group consisting of prematurity, IUGR, meconium passage, placental abruption, multiple gestation, and fetal infection resulting in the fetal inflammatory response syndrome.

9. The apparatus of claim 1, wherein the at least one computer is operative to determine when maternal uterine activity exhibits at least one non-reassuring characteristic independent of fetal response.

10. The apparatus of claim 1, wherein the at least one non-reassuring characteristic for each of the parameters (a) through (e) is selected from the following: (a) for FHR: any of (i) a fetal heart rate of over 160 bpm or (ii) a fetal heart rate of less than 120 bpm; (b) for baseline FHR variability: any of (i) a variability of more than 15 bpm or (ii) a variability of less than 5 bpm; (c) for FHR accelerations: any of (i) the occurrence of less than two accelerations in 10 minutes of 15 bpm for at least 15 seconds, (ii) the absence of shoulders, or (iii) the presence of overshoots; (d) for FHR decelerations: any of (i) late decelerations, (ii) variable decelerations with slow return to baseline FHR, (iii) the presence of overshoots, or (iv) prolonged FHR deceleration; and (e) for maternal uterine activity: any of (i) repetitive contractions in excess of 5 uterine contractions in 3 consecutive 10 minute windows, (ii) a uterine resting tone of greater than 25 mm Hg, (iii) a contraction duration of greater than 90 seconds, (iv) the coupling or tripling of contractions prior to return to baseline, or (v) a contraction duty cycle of greater than 50%.

11. The apparatus of claim 1, wherein the highest determined level of risk to the fetus corresponds to any combination of a number of the parameters (a) through (e) that simultaneously, independently exhibit at least one non-reassuring characteristic and a number of the identified number of one or more antecedent clinical parameters which together total six.

12. The apparatus of claim 1, wherein the one or more antecedent clinical parameters are genetic, proteomic, and metabolic markers correlated to a higher risk of neonatal encephalopathy and cerebral palsy.

13. An apparatus for identifying the level of fetal risk during labor, comprising:
at least one computer operative to receive input signals indicative of at least fetal heart rate ("FHR") and maternal uterine activity in a patient, the at least one computer further operative (i) to determine from the FHR at least baseline FHR variability, FHR accelerations, and FHR decelerations, and (ii) to determine when each of at least (a) FHR, (b) baseline FHR variability, (c) FHR accelerations, (d) FHR decelerations, and (e) maternal uterine activity exhibit at least one non-reassuring characteristic from among a plurality of pre-defined non-reassuring characteristics for at least the parameters (a) through (e); and
wherein the at least one computer is further operative to (iii) to receive user-inputs indicative of the presence in the patient of the concurrent clinical parameters of (f) prolonged latent phase, (g) arrest and protraction of the active phase, (h) failed descent of the presenting part, (i) arrested descent of the presenting part, and (j) protracted descent of the presenting part, and (iv) to determine at a given point in time during labor a present level of risk to the fetus which takes into account only:
the total of the number of the parameters (a) through (e) that each simultaneously, independently exhibit at least one of the non-reassuring characteristics at the given point in time during labor; and
the number of the concurrent clinical parameters (f) through (j) that are simultaneously present;
wherein the at least one computer is further operative to indicate a predetermined action to be taken in response to the present level of risk to the fetus, and wherein further the indicated predetermined action is intervention in labor when the present level of risk to the fetus for an adverse outcome is at a predetermined level; and
at least one output operatively connected to the at least one computer, the at least one output indicating the determined present level of risk to the fetus and the predetermined action to be taken in response to the indicated present level of risk to the fetus.

14. The apparatus of claim 13, wherein the at least one computer is further operative to receive user-inputs indicative of the presence in a patient of one or more antecedent clinical parameters which elevate the level of fetal risk during labor, and is operative to determine a present level of risk to the fetus corresponding to the total number of the one or more antecedent clinical parameters which elevate the level of fetal risk during labor and the number of the said parameters (a) through (e) that simultaneously, independently exhibit at least one non-reassuring characteristic.

15. The apparatus of claim 14, wherein the one or more antecedent clinical parameters are maternal antecedent clinical parameters.

16. The apparatus of claim 15, wherein the maternal antecedent clinical parameters are one or more from the group consisting of hypertension, anemia, hemoglobinopathies, cardiac dysfunction, and maternal pulmonary disorders.

17. The apparatus of claim 14, wherein the one or more antecedent clinical parameters are fetal antecedent clinical parameters.

18. The apparatus of claim 17, wherein the fetal antecedent clinical parameters are one or more from the group consisting of prematurity, IUGR, meconium passage, placental abruption, multiple gestation, and fetal infection resulting in the fetal inflammatory response syndrome.

19. The apparatus of claim 14, wherein the one or more antecedent clinical parameters are genetic, proteomic, and metabolic markers correlated to a higher risk of neonatal encephalopathy and cerebral palsy.

20. The apparatus of claim 13, wherein the highest determined level of risk to the fetus corresponds to any combination of a number of the parameters (a) through (e) that simultaneously, independently exhibit at least one non-reassuring characteristic and a number of the concurrent clinical parameters (f) through (j) that are simultaneously present in the patient which together total six.

21. The apparatus of claim 20, wherein the at least one computer is further operative to identify a predetermined action to be taken in response to the indicated present level of risk to the fetus.

22. The apparatus of claim 13, wherein the at least one computer is operative to determine when maternal uterine activity exhibits at least one non-reassuring characteristic independent of fetal response.

23. The apparatus of claim 13, wherein the at least one non-reassuring characteristic for each of the parameters (a) through (e) is selected from the following: (a) for FHR: any of (i) a fetal heart rate of over 160 bpm or (ii) a fetal heart rate of less than 120 bpm; (b) for baseline FHR variability: any of (i) a variability of more than 15 bpm or (ii) a variability of less than 5 bpm; (c) for FHR accelerations: any of (i) the occurrence of less than two accelerations in 10 minutes of 15 bpm for at least 15 seconds, (ii) the absence of shoulders, or (iii) the presence of overshoots; (d) for FHR decelerations: any of (i) late decelerations, (ii) variable decelerations with slow return to baseline FHR, (iii) the presence of overshoots, or (iv) prolonged FHR deceleration; and (e) for maternal uterine activity: any of (i) repetitive contractions in excess of 5 uterine contractions in 3 consecutive 10 minute windows, (ii) a uterine resting tone of greater than 25 mm Hg, (iii) a contraction duration of greater than 90 seconds, (iv) the coupling or tripling of contractions prior to return to baseline, or (v) a contraction duty cycle of greater than 50%.

24. The apparatus of claim 13, wherein the at least one computer is further operative to identify a predetermined action to be taken in response to the indicated present level of risk to the fetus.

25. An apparatus for identifying the level of fetal risk during labor, comprising:
- at least one computer operative to receive input signals indicative of at least fetal heart rate ("FHR") and maternal uterine activity in a patient, the at least one computer further operative:
  - (i) to determine from the FHR at least baseline FHR variability, FHR accelerations, and FHR decelerations;
  - (ii) to determine when each of at least (a) FHR, (b) baseline FHR variability, (c) FHR accelerations, (d) FHR decelerations, and (e) maternal uterine activity exhibit at least one non-reassuring characteristic from among a plurality of pre-defined non-reassuring characteristics for at least the parameters (a) through (e), and to assign a pre-defined value to each of said parameters (a) through (e) that simultaneously, independently exhibit at least one of the non-reassuring characteristics; and
  - (iii) to determine, at a given point in time during labor, a present level of risk to the fetus corresponding only to the total of the values assigned to each of said parameters (a) through (e) at the given point in time; and
- wherein the at least one computer is further operative to indicate a predetermined action to be taken in response to the present level of risk to the fetus, and wherein further the indicated predetermined action is intervention in labor when the present level of risk to the fetus for an adverse outcome is at a predetermined level; and
- at least one output operatively connected to the at least one computer, the at least one output indicating the determined present level of risk to the fetus and the predetermined action to be taken in response to the indicated present level of risk to the fetus.

* * * * *